(12) United States Patent
Gobbi et al.

(10) Patent No.: US 7,939,535 B2
(45) Date of Patent: May 10, 2011

(54) BENZO[D]ISOXAZOL-3-YL-PIPERAZIN DERIVATIVES USEFUL AS MODULATORS OF DOPAMINE D3 RECEPTORS

(75) Inventors: Luca Gobbi, Muttenz (CH); Georg Jaeschke, Basel (CH); Rosa Maria Rodriguez Sarmiento, Basel (CH); Lucinda Steward, Basel (CH)

(73) Assignee: Hoffman-La Roche Inc., Nutley, NJ (US)

( * ) Notice: Subject to any disclaimer, the term of this patent is extended or adjusted under 35 U.S.C. 154(b) by 50 days.

(21) Appl. No.: 12/560,471

(22) Filed: Sep. 16, 2009

(65) Prior Publication Data

US 2010/0075985 A1    Mar. 25, 2010

(30) Foreign Application Priority Data

Sep. 23, 2008  (EP) .................................... 08164903

(51) Int. Cl.
*A61K 31/497* (2006.01)
*C07D 419/04* (2006.01)
(52) U.S. Cl. .................. 514/254.04; 544/368
(58) Field of Classification Search .................. 544/368; 514/254.04
See application file for complete search history.

(56) References Cited

U.S. PATENT DOCUMENTS 7,825,123 B2 * 11/2010 Gobbi et al. ............. 514/253.04

FOREIGN PATENT DOCUMENTS

WO    WO 2004/026864    4/2004

OTHER PUBLICATIONS

Leopoldo M et al *Jour. of Med. Chem.* (2002), 45:5627-5735.
Missale et al., Physiol. Rev. vol. 78 pp. 189-225 (1998).
Gurevich E. V., Neuropsychopharmacology vol. 20 pp. 60-80 (1999).
Joyce J. N., Drug Discovery Today 1, vol. 10, No. 13 pp. 917-925 (2005).
Gurevich E.V., Arch. Gen. Psychiatry vol. 54 pp. 225-232 (1997).
Knutsen et al., Biorg. Med. Chem. Lett. vol. 17 (2007) pp. 662-667.

* cited by examiner

*Primary Examiner* — James O Wilson
*Assistant Examiner* — Ebenezer Sackey
(74) *Attorney, Agent, or Firm* — George W. Johnston; Patricia S. Rocha-Tramaloni; Kimberly J. Prior

(57) ABSTRACT

The present invention provides compounds of the general formula (I), having affinity and selectivity for the dopamine D3 receptors, their manufacture, pharmaceutical compositions containing them and their use for the therapeutic and/or prophylactic treatment of cognitive disorders.

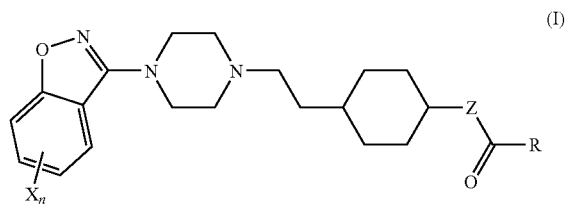

59 Claims, No Drawings

BENZO[D]ISOXAZOL-3-YL-PIPERAZIN DERIVATIVES USEFUL AS MODULATORS OF DOPAMINE D3 RECEPTORS

PRIORITY TO RELATED APPLICATION(S)

This application claims the benefit of European Patent Application No. 08164903.0, filed Sep. 23, 2008, which is hereby incorporated by reference in its entirety.

BACKGROUND INFORMATION

Dopamine, a major catecholamine neurotransmitter, is involved in the regulation of a variety of functions which include emotion, cognition, motor functions, and positive reinforcement, (Purves, D. et al. (2004) Neuroscience. Sinauer, third edition, Sunderland, Mass.).

The biological activities of dopamine are mediated through G protein-coupled receptors (GPCRs) and in human, five different dopamine receptors $D_1$-$D_5$ have been identified, where the $D_2$-like receptors ($D_2$, $D_3$ and $D_4$) couple to the G-protein $G_{\alpha I}$ (Missale, C. et al. (1998) Dopamine receptors: from structure to function. Physiol. Rev. 78, 189-225). The $D_3$ dopamine receptor is most highly expressed in the nucleus accumbens (Gurevich, E. V., Joyce, J. N. (1999) Distribution of dopamine D3 receptor expressing neurons in the human forebrain: comparison with D2 receptor expressing neurons. Neuropsychopharmacology 20, 60-80), and is proposed to modulate the mesolimbic pathway consisting of neuronal projections from the ventral tegmental area, hippocampus and amygdala to the nucleus accumbens, which projects to the prefrontal and cingulate cortices as well as various thalamic nuclei. The limbic circuit is thought to be important for emotional behavior and thus $D_3$ receptor antagonists are proposed to modulate psychotic symptoms such as hallucinations, delusions and thought disorder (Joyce, J. N. and Millan, M. J., (2005) Dopamine D3 receptor antagonists as therapeutic agents. Drug Discovery Today, 1 July, Vol. 10, No. 13, 917-25), while these antagonists spare the $D_2$ modulated striatal extrapyramidal system (associated with EPS induction). In addition, it has been reported that drug naive schizophrenic patients show altered levels of $D_3$ receptor expression (Gurevich, E. V. et al. (1997) Mesolimbic dopamine D3 receptors and use of antipsychotics in patients with schizophrenia. A postmortem study. Arch. Gen. Psychiatry 54, 225-232) and dopamine release (Laruelle, M. (2000) (2000) Imaging dopamine dysregulation in schizophrenia: implication for treatment. Presented at Workshop Schizophr.: Pathol. Bases and Mech. Antipsychotic Action, Chicago), indicating that a disturbed homeostasis of dopamine plays an important role in the etiology of schizophrenic symptoms.

SUMMARY OF THE INVENTION

The present invention provides compounds of formula (I),

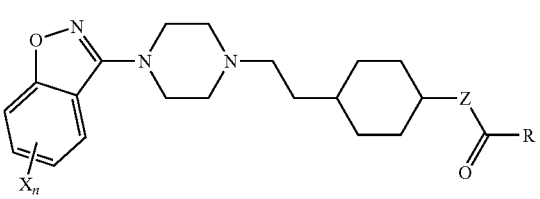

(I)

wherein:
X is independently fluorine or chlorine;
n is 1 or 2;
Z is —NH— or —O—;
R is $C_{1-6}$-alkyl, wherein $C_{1-6}$-alkyl is optionally substituted by —$CONH_2$, 3 to 6 membered monocyclic cycloalkyl or 4 to 6 membered monocyclic heterocycloalkyl;
$C_{1-6}$-hydroxyalkyl;
$C_{1-6}$-alkoxy;
3 to 6 membered monocyclic cycloalkyl; or
4 to 6 membered monocyclic heterocycloalkyl;
wherein 3 to 6 membered monocyclic cycloalkyl and 4 to 6 membered monocyclic heterocycloalkyl are optionally substituted by one or more substituents selected from the group consisting of halo, hydroxy, $C_{1-6}$-alkyl, $C_{1-6}$-hydroxyallyl and $C_{1-6}$-alkoxy; as well as pharmaceutically acceptable salts thereof.

Compounds of formula (I) have affinity for dopamine D3 receptors and thus are useful in the treatment of conditions wherein modulation, especially antagonism/inhibition, of D3 receptors is beneficial, e.g. to treat drug dependency or as antipsychotic agents.

DETAILED DESCRIPTION OF THE INVENTION

Compounds of formula (I) and their pharmaceutically acceptable salts are useful in the treatment of all aspects of drug dependency, including drug intake, relapse to drug-seeking behaviour following abstinence and withdrawal symptoms from drugs of abuse such as alcohol, cocaine, opiates, nicotine, benzodiazepines and inhibition of tolerance induced by opioids, as well as for the treatment of drug craving. They also are useful as an antipsychotic agents for example in the treatment of schizophrenia, schizo-affective disorders, schizophreniform diseases, psychotic depression (which term includes bipolar depression, unipolar depression, single or recurrent major depressive episodes with or without psychotic features, catatonic features, melancholic features, atypical features or postpartum onset, seasonal affective disorder and dysthymia, depressive disorders resulting from a general medical condition including, but not limited to, myocardial infarction, diabetes, miscarriage or abortion), anxiety disorders (which includes generalised anxiety and social anxiety disorder), mania, acute mania, paranoid and delusional disorders. The compounds are also useful for the treatment of a family of related disorders referred to as somatoform disorders, as well as for the treatment of premature ejaculation.

The compounds are further useful for the treatment of attention-deficit hyperactivity disorder (ADHD), addiction (smoking cessation, cocaine and others) and obsessive compulsive disorder (OCD).

Compounds of formula (I) can form acid addition salts with acids, such as conventional pharmaceutically acceptable acids, for example hydrochloride, hydrobromide, phosphate, acetate, fumarate, maleate, salicylate, sulphate, pyruvate, citrate, lactate, mandelate, tartarate, and methanesulphonate. Preferred are the hydrochloride salts. Also solvates and hydrates of compounds of formula (I) and their salts form part of the present invention.

Compounds of formula (I) can have one or more asymmetric carbon atom and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated, that the compounds of formula (I) in this invention can be derivatized at functional groups to provide derivatives that are capable of conversion back to the parent compound in vivo. Physiologically acceptable and metabolically labile derivatives, that are capable of producing the parent compounds of formula (I) in vivo are also within the scope of this invention.

As used herein, the term "$C_{1-6}$-alkyl" denotes monovalent linear or branched saturated hydrocarbon moiety, consisting solely of carbon and hydrogen atoms, having from 1 to 6 carbon atoms, for example, methyl, ethyl, propyl, isopropyl, n-butyl, iso-butyl, sec-butyl, tert-butyl and the like. Preferred alkyl groups are groups with 1, 2, 3 or 4 carbon atoms. Most preferred alkyl groups are methyl and ethyl.

$C_{1-6}$-alkyl is optionally substituted by —$CONH_2$, 3 to 6 membered monocyclic cycloalkyl or 4 to 6 membered monocyclic heterocycloalkyl. Preferred $C_{1-6}$-alkyl substituted by —$CONH_2$, 3 to 6 membered monocyclic cycloalkyl or 4 to 6 membered monocyclic heterocycloalkyl is preferably $CONH_2$-methyl, cyclopropyl-methyl and methoxy-cyclohexyl-methyl.

The term "halogen" denotes chlorine (chloro, Cl), iodine (iodo, I), fluorine (fluoro, F) and bromine (bromo, Br). Preferred halogen are fluoro, chloro and bromo, more preferred are fluoro and chloro, most preferred is fluoro.

The term "$C_{1-6}$-alkoxy" denotes a group —O—R' wherein R' is $C_{1-6}$-alkyl as defined above. Preferred is methoxy-ethyl.

The term "$C_{1-6}$-haloalkyl" denotes an alkyl group as defined above wherein at least one of the hydrogen atoms of the alkyl group is replaced by a halogen atom, preferably fluoro or chloro, most preferably fluoro. Examples of haloalkyl include but are not limited to methyl, ethyl, propyl, isopropyl, isobutyl, sec-butyl, tert-butyl, pentyl or n-hexyl wherein one or more hydrogen atoms are replaced by Cl, F, Br or I atom(s), as well as those haloalkyl groups specifically illustrated by the examples herein below. Among the preferred haloalkyl groups are monofluoro-, difluoro- or trifluoro-methyl, ethyl or -propyl, for example 3,3,3-trifluoro-propyl, 2-fluoroethyl, 2,2,2-trifluoroethyl, fluoromethyl, trifluoromethyl. Preferred is fluoromethyl.

The term "$C_{1-6}$-hydroxyalkyl" denotes a group HO—R" wherein R" is $C_{1-6}$-alkyl as defined above. Preferred is hydroxy-methyl.

The phrase "3 to 6 membered monocyclic cycloalkyl" refers to a monovalent saturated monocyclic hydrocarbon radical of 3 to 6 ring carbon atoms. Examples are cyclopropyl, cyclobutanyl, cyclopentyl or cyclohexyl. Preferred examples are cyclopropyl, cyclopentyl and cyclohexyl. Most preferred is cyclopropyl.

The phrase "4 to 6 membered monocyclic heterocycloalkyl" refers to a monovalent saturated 4- to 6-membered monocyclic ring system containing one, two or three ring heteroatoms selected from N, O and S, the remaining ring atoms being carbon atoms. 5- or 6-membered monocyclic heterocycloalkyls are preferred. "Heterocycloalkyl" can be unsubstituted or substituted as described herein. Preferred is tetrahydropyranyl.

"Pharmaceutically acceptable," such as pharmaceutically acceptable carrier, excipient, etc., means pharmacologically acceptable and substantially non-toxic to the subject to which the particular compound is administered.

The terms "pharmaceutically acceptable salt" and "pharmaceutically acceptable acid addition salts" embrace salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

When indicating the number of substituents, the term "one or more" means from one substituent to the highest possible number of substitution, i.e. replacement of one hydrogen up to replacement of all hydrogens by substituents. Thereby, one, two or three substituents are preferred.

In detail, the present invention provides compounds of formula (I),

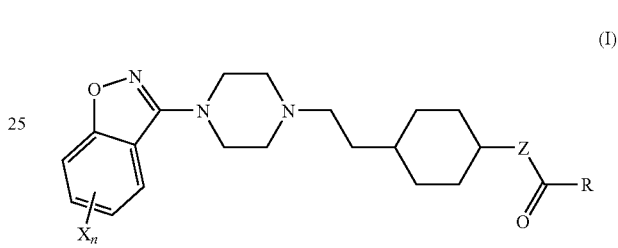

wherein:

X is independently fluorine or chlorine;

n is 1 or 2;

Z is —NH— or —O—;

R is $C_{1-6}$-allyl, wherein $C_{1-6}$-alkyl is optionally substituted by —$CONH_2$, 3 to 6 membered monocyclic cycloalkyl or 4 to 6 membered monocyclic heterocycloallyl;

$C_{1-6}$-hydroxyalkyl;

$C_{1-6}$-alkoxy;

3 to 6 membered monocyclic cycloalkyl; or 4 to 6 membered monocyclic heterocycloalkyl;

wherein 3 to 6 membered monocyclic cycloalkyl and 4 to 6 membered monocyclic heterocycloalkyl are optionally substituted by one or more substituents selected from the group consisting of halo, hydroxy, $C_{1-6}$-alkyl, $C_{1-6}$-haloalkyl, $C_{1-6}$-hydroxyalkyl and $C_{1-6}$-alkoxy; as well as pharmaceutically acceptable salts thereof.

In a preferred embodiment the present invention relates to a compound of formula (I'),

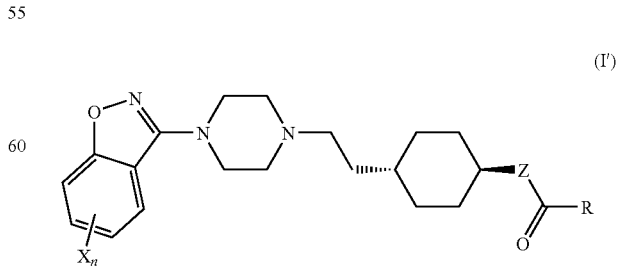

wherein R, X, Z and n are defined as given above.

Special preference is given to compounds of formulae (Ia) or (Ia'):

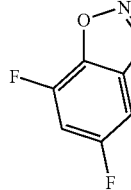
(Ia)

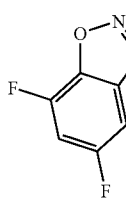
(Ia')

wherein Z and R are defined as given above.

Special preference is given to a compound of formula (Ia') selected from the group consisting of:

N-(trans-4-{2-[4-(5,7-Difluoro-benzo[d]isoxazol-3-yl)-piperazin-1-yl]-ethyl}-cyclohexyl)-acetamide;

N-(trans-4-{2-[4-(5,7-Difluoro-benzo[d]isoxazol-3-yl)-piperazin-1-yl]-ethyl}-cyclohexyl)-2-hydroxy-acetamide;

N-(trans-4-{2-[4-(5,7-Difluoro-benzo[d]isoxazol-3-yl)-piperazin-1-yl]-ethyl}-cyclohexyl)-2-methoxy-acetamide;

N-(trans-4-{2-[4-(5,7-Difluoro-benzo[d]isoxazol-3-yl)-piperazin-1-yl]-ethyl}-cyclohexyl)-3-methoxy-propionamide;

N-(trans-4-{2-[4-(5,7-Difluoro-benzo[d]isoxazol-3-yl)-piperazin-1-yl]-ethyl}-cyclohexyl)-2-(trans-4-methoxy-cyclohexyl)-acetamide;

N-(trans-4-{2-[4-(5,7-Difluoro-benzo[d]isoxazol-3-yl)-piperazin-1-yl]-ethyl}-cyclohexyl)-propionamide;

2-Cyclopropyl-N-(trans-4-{2-[4-(5,7-difluoro-benzo[d]isoxazol-3-yl)-piperazin-1-yl]-ethyl}-cyclohexyl)-acetamide;

Tetrahydro-pyran-4-carboxylic acid (trans-4-{2-[4-(5,7-difluoro-benzo[d]isoxazol-3-yl)-piperazin-1-yl]-ethyl}-cyclohexyl)-amide; and N-(trans-4-{2-[4-(5,7-Difluoro-benzo[d]isoxazol-3-yl)-piperazin-1-yl]-ethyl}-cyclohexyl)-malonamide.

Special preference is given to compounds of formulae (Ib) or (Ib'):

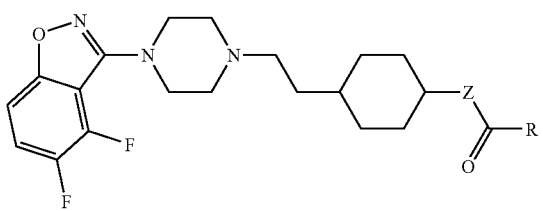
(Ib)

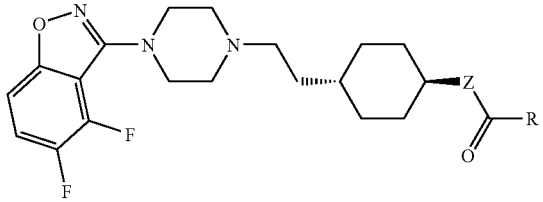
(Ib')

wherein Z and R are defined as given above.

Special preference is given to a compound of formula (Ib') selected from the group consisting of:

N-(trans-4-{2-[4-(4,5-Difluoro-benzo[d]isoxazol-3-yl)-piperazin-1-yl]-ethyl}-cyclohexyl)-acetamide and N-(trans-4-{2-[4-(4,5-Difluoro-benzo[d]isoxazol-3-yl)-piperazin-1-yl]-ethyl}-cyclohexyl)-3-methoxy-propionamide.

In one embodiment, the invention provides compounds of formula (I) wherein each X is independently fluorine or chlorine.

In one embodiment, the invention provides compounds of formula (I) wherein X is fluorine.

In one embodiment, the invention provides compounds of formula (I) wherein X is chlorine.

In one embodiment, the invention provides compounds of formula (I) wherein n is 1 or 2.

In one embodiment, the invention provides compounds of formula (I) wherein n is 1.

In one embodiment, the invention provides compounds of formula (I) wherein n is 2.

In one embodiment, the invention provides compounds of formulae I, Ia, Ia', Ib, Ib' wherein Z is —NH— or —O—.

In one embodiment, the invention provides compounds of formulae I, Ia, Ia', Ib, Ib' wherein Z is —NH—.

In one embodiment, the invention provides compounds of formulae I, Ia, Ia', Ib, Ib' wherein Z is —O—.

In one embodiment, the invention provides compounds of formulae I, Ia, Ia', Ib, Ib' wherein R is $C_{1-6}$-alkyl, wherein $C_{1-6}$-alkyl is optionally substituted by —$CONH_2$, 3 to 6 membered monocyclic cycloalkyl or 4 to 6 membered monocyclic heterocycloalkyl;

$C_{1-6}$-hydroxyalkyl;

$C_{1-6}$-alkoxy;

3 to 6 membered monocyclic cycloalkyl; or 4 to 6 membered monocyclic heterocycloalkyl;

wherein 3 to 6 membered monocyclic cycloalkyl and 4 to 6 membered monocyclic heterocycloalkyl are optionally substituted by one or more substituents selected from the group consisting of halo, hydroxy, $C_{1-6}$-alkyl, $C_{1-6}$-haloalkyl, $C_{1-6}$-hydroxyalkyl and $C_{1-6}$-alkoxy.

In one embodiment, the invention provides compounds of formulae I, Ia, Ia', Ib, Ib' wherein R is methyl, hydroxymethyl, methoxy-methyl, methoxy-ethyl, methoxy-cyclohexyl-methyl, ethyl, cyclopropyl-methyl, tetrahydropyranyl or $CONH_2$-methyl.

In one embodiment, the invention provides compounds of formulae I, Ia, Ia', Ib, Ib' wherein R is $C_{1-6}$-alkyl.

In one embodiment, the invention provides compounds of formulae I, Ia, Ia', Ib, Ib' wherein R is methyl.

In one embodiment, the invention provides compounds of formulae I, Ia, Ia', Ib, Ib' wherein R is ethyl.

In one embodiment, the invention provides compounds of formulae I, Ia, Ia', Ib, Ib' wherein R $C_{1-6}$-alkyl optionally substituted by —CONH$_2$, 3 to 6 membered monocyclic cycloalkyl or 4 to 6 membered monocyclic heterocycloalkyl.

In one embodiment, the invention provides compounds of formulae I, Ia, Ia', Ib, Ib' wherein R C$_{1-6}$-alkyl substituted by —CONH$_2$, 3 to 6 membered monocyclic cycloalkyl or 4 to 6 membered monocyclic heterocycloalkyl.

In one embodiment, the invention provides compounds of formulae I, Ia, Ia', Ib, Ib' wherein R is C$_{1-6}$-alkyl substituted by —CONH$_2$.

In one embodiment, the invention provides compounds of formulae I, Ia, Ia', Ib, Ib' wherein R is CONH$_2$-methyl.

In one embodiment, the invention provides compounds of formulae I, Ia, Ia', Ib, Ib' wherein R is C$_{1-6}$-alkyl substituted by 3 to 6 membered monocyclic cycloalkyl.

In one embodiment, the invention provides compounds of formulae I, Ia, Ia', Ib, Ib' wherein R is cyclopropyl-methyl.

In one embodiment, the invention provides compounds of formulae I, Ia, Ia', Ib, Ib' wherein R is C$_{1-6}$-alkyl substituted by 3 to 6 membered monocyclic cycloalkyl wherein the 3 to 6 membered monocyclic cycloalkyl substituted by one or more substituents selected from the group consisting of halo, hydroxy, C$_{1-6}$-alkyl, C$_{1-6}$-haloalkyl, C$_{1-6}$-hydroxyalkyl and C$_{1-6}$-alkoxy.

In one embodiment, the invention provides compounds of formulae I, Ia, Ia', Ib, Ib' wherein R is C$_{1-6}$-alkyl substituted by 3 to 6 membered monocyclic cycloalkyl, which 3 to 6 membered monocyclic cycloalkyl is substituted by halo.

In one embodiment, the invention provides compounds of formulae I, Ia, Ia', Ib, Ib' wherein R is C$_{1-6}$-alkyl substituted by 3 to 6 membered monocyclic cycloalkyl, which 3 to 6 membered monocyclic cycloalkyl is substituted by hydroxy.

In one embodiment, the invention provides compounds of formulae I, Ia, Ia', Ib, Ib' wherein R is methoxy-cyclohexyl-methyl.

In one embodiment, the invention provides compounds of formulae I, Ia, Ia', Ib, Ib' wherein R is C$_{1-6}$-alkyl substituted by 3 to 6 membered monocyclic cycloalkyl, which 3 to 6 membered monocyclic cycloalkyl is substituted by C$_{1-6}$-alkyl.

In one embodiment, the invention provides compounds of formulae I, Ia, Ia', Ib, Ib' wherein R is C$_{1-6}$-alkyl substituted by 3 to 6 membered monocyclic cycloalkyl, which 3 to 6 membered monocyclic cycloalkyl is substituted by C$_{1-6}$-haloalkyl.

In one embodiment, the invention provides compounds of formulae I, Ia, Ia', Ib, Ib' wherein R is C$_{1-6}$-alkyl substituted by 3 to 6 membered monocyclic cycloalkyl, which 3 to 6 membered monocyclic cycloalkyl is substituted by C$_{1-6}$-hydroxyalkyl.

In one embodiment, the invention provides compounds of formulae I, Ia, Ia', Ib, Ib' wherein R is C$_{1-6}$-alkyl substituted by 3 to 6 membered monocyclic cycloalkyl, which 3 to 6 membered monocyclic cycloalkyl is substituted by C$_{1-6}$-alkoxy.

In one embodiment, the invention provides compounds of formulae I, Ia, Ia', Ib, Ib' wherein R is C$_{1-6}$-alkyl substituted by 4 to 6 membered monocyclic heterocycloalkyl wherein the 4 to 6 membered monocyclic heterocycloalkyl substituted by one or more substituents selected from the group consisting of halo, hydroxy, C$_{1-6}$-alkyl, C$_{1-6}$-haloalkyl, C$_{1-6}$-hydroxyalkyl and C$_{1-6}$-alkoxy.

In one embodiment, the invention provides compounds of formulae I, Ia, Ia', Ib, Ib' wherein R is C$_{1-6}$-alkyl substituted by 4 to 6 membered monocyclic heterocycloalkyl, which 4 to 6 membered monocyclic heterocycloalkyl is substituted by halo.

In one embodiment, the invention provides compounds of formulae I, Ia, Ia', Ib, Ib' wherein R is C$_{1-6}$-alkyl substituted by 4 to 6 membered monocyclic heterocycloalkyl, which 4 to 6 membered monocyclic heterocycloalkyl is substituted by hydroxy.

In one embodiment, the invention provides compounds of formulae I, Ia, Ia', Ib, Ib' wherein R is C$_{1-6}$-alkyl substituted by 4 to 6 membered monocyclic heterocycloalkyl, which 4 to 6 membered monocyclic heterocycloalkyl is substituted by C$_{1-6}$-alkyl.

In one embodiment, the invention provides compounds of formulae I, Ia, Ia', Ib, Ib' wherein R is C$_{1-6}$-alkyl substituted by 4 to 6 membered monocyclic heterocycloalkyl, which 4 to 6 membered monocyclic heterocycloalkyl is substituted by C$_{1-6}$-haloalkyl.

In one embodiment, the invention provides compounds of formulae I, Ia, Ia', Ib, Ib' wherein R is C$_{1-6}$-alkyl substituted by 4 to 6 membered monocyclic heterocycloalkyl, which 4 to 6 membered monocyclic heterocycloalkyl is substituted by C$_{1-6}$-hydroxyalkyl.

In one embodiment, the invention provides compounds of formulae I, Ia, Ia', Ib, Ib' wherein R is C$_{1-6}$-alkyl substituted by 4 to 6 membered monocyclic heterocycloalkyl, which 4 to 6 membered monocyclic heterocycloalkyl is substituted by C$_{1-6}$-alkoxy.

In one embodiment, the invention provides compounds of formulae I, Ia, Ia', Ib, Ib' wherein R is C$_{1-6}$-alkyl substituted by 4 to 6 membered monocyclic heterocycloalkyl.

In one embodiment, the invention provides compounds of formulae I, Ia, Ia', Ib, Ib' wherein R is C$_{1-6}$-hydroxyalkyl.

In one embodiment, the invention provides compounds of formulae I, Ia, Ia', Ib, Ib' wherein R is C$_{1-6}$-alkoxy.

In one embodiment, the invention provides compounds of formulae I, Ia, Ia', Ib, Ib' wherein R is 3 to 6 membered monocyclic cycloalkyl.

In one embodiment, the invention provides compounds of formulae I, Ia, Ia', Ib, Ib' wherein R is 3 to 6 membered monocyclic cycloalkyl substituted by one or more substituents selected from the group consisting of halo, hydroxy, C$_{1-6}$-alkyl, C$_{1-6}$-haloalkyl, C$_{1-6}$-hydroxyalkyl and C$_{1-6}$-alkoxy.

In one embodiment, the invention provides compounds of formulae I, Ia, Ia', Ib, Ib' wherein R is 3 to 6 membered monocyclic cycloalkyl, which 3 to 6 membered monocyclic cycloalkyl is substituted by halo.

In one embodiment, the invention provides compounds of formulae I, Ia, Ia', Ib, Ib' wherein R is 3 to 6 membered monocyclic cycloalkyl, which 3 to 6 membered monocyclic cycloalkyl is substituted by hydroxy.

In one embodiment, the invention provides compounds of formulae I, Ia, Ia', Ib, Ib' wherein R is 3 to 6 membered monocyclic cycloalkyl, which 3 to 6 membered monocyclic cycloalkyl is substituted by C$_{1-6}$-alkyl.

In one embodiment, the invention provides compounds of formulae I, Ia, Ia', Ib, Ib' wherein R is 3 to 6 membered monocyclic cycloalkyl, which 3 to 6 membered monocyclic cycloalkyl is substituted by C$_{1-6}$-haloalkyl.

In one embodiment, the invention provides compounds of formulae I, Ia, Ia', Ib, Ib' wherein R is 3 to 6 membered monocyclic cycloalkyl, which 3 to 6 membered monocyclic cycloalkyl is substituted by C$_{1-6}$-hydroxyalkyl.

In one embodiment, the invention provides compounds of formulae I, Ia, Ia', Ib, Ib' wherein R is 3 to 6 membered monocyclic cycloalkyl, which 3 to 6 membered monocyclic cycloalkyl is substituted by C$_{1-6}$-alkoxy.

In one embodiment, the invention provides compounds of formulae I, Ia, Ia', Ib, Ib' wherein R is 4 to 6 membered monocyclic heterocycloalkyl substituted by one or more substituents selected from the group consisting of halo, hydroxy, $C_{1-6}$-alkyl, $C_{1-6}$-haloalkyl, $C_{1-6}$-hydroxyalkyl and $C_{1-6}$-alkoxy.

In one embodiment, the invention provides compounds of formulae I, Ia, Ia', Ib, Ib' wherein R is 4 to 6 membered monocyclic heterocycloalkyl, which 4 to 6 membered monocyclic heterocycloalkyl is substituted by halo.

In one embodiment, the invention provides compounds of formulae I, Ia, Ia', Ib, Ib' wherein R is 4 to 6 membered monocyclic heterocycloalkyl, which 4 to 6 membered monocyclic heterocycloalkyl is substituted by hydroxy.

In one embodiment, the invention provides compounds of formulae I, Ia, Ia', Ib, Ib' wherein R is 4 to 6 membered monocyclic heterocycloalkyl, which 4 to 6 membered monocyclic heterocycloalkyl is substituted by $C_{1-6}$-alkyl.

In one embodiment, the invention provides compounds of formulae I, Ia, Ia', Ib, Ib' wherein R is 4 to 6 membered monocyclic heterocycloalkyl, which 4 to 6 membered monocyclic heterocycloalkyl is substituted by $C_{1-6}$-haloalkyl.

In one embodiment, the invention provides compounds of formulae I, Ia, Ia', Ib, Ib' wherein R is 4 to 6 membered monocyclic heterocycloalkyl, which 4 to 6 membered monocyclic heterocycloalkyl is substituted by $C_{1-5}$-hydroxyalkyl.

In one embodiment, the invention provides compounds of formulae I, Ia, Ib, Ib' wherein R is 4 to 6 membered monocyclic heterocycloalkyl, which 4 to 6 membered monocyclic heterocycloalkyl is substituted by $C_{1-6}$-alkoxy.

In one embodiment, the invention provides compounds of formulae I, Ia, Ia', Ib, Ib' wherein R is 4 to 6 membered monocyclic heterocycloalkyl.

A further aspect, the present invention provides pharmaceutical compositions containing a therapeutically effective amount of a compound of formulae I, Ia, Ia', Ib, Ib' or a pharmaceutically acceptable salt thereof and a pharmaceutically acceptable carrier.

In another aspect, the present invention provides a method for the treatment and/or prevention of cognitive disorders, drug addition, depression, anxiety, drug dependence, dementias, memory impairment, psychotic depression, psychoses comprising paranoia and delusions, attention deficit hyperactivity disorder, addition and obsessive compulsive disorder which comprises administering a therapeutically effective amount of a compound of formula I, Ia, Ia', Ib, IB', or a pharmaceutically acceptable salt thereof.

A further aspect of the present invention provides pharmaceutical compositions containing the compounds of formulae I, Ia, Ia', Ib, Ib' for the treatment of schizophrenia, cognitive disorders and drug addiction.

A further aspect of the present invention provides the process for the manufacture of compounds of formulae I, Ia, Ia', Ib, Ib' as defined above.

A further aspect of the present invention provides compound of formula (I) for the treatment or prevention of diseases related to the D3 receptor.

A further aspect of the present invention provides a method for the therapeutic and/or prophylactic treatment of a disorder or condition mediated by the D3 receptor binding site, or that can be treated via modulation of the D3 receptor binding site, particularly for the therapeutic and/or prophylactic treatment of cognitive disorders, drug addiction, depression, anxiety, drug dependence, dementias, memory impairment, psychotic disorders comprising schizophrenia, schizoaffective disorders, bipolar disease, mania, psychotic depression, psychoses comprising paranoia and delusions, attention-deficit hyperactivity disorder, addiction and obsessive compulsive disorder, which method comprises administering a compound of formula (I) to a human being or animal.

The preparation of compounds of formula (I) of the present invention can be carried out in sequential or convergent synthetic routes. Syntheses of the invention are shown in the following schemes. The skills required for carrying out the reaction and purification of the resulting products are known to those skilled in the art. The substituents and indices used in the following description of the processes have the significance given herein before unless indicated to the contrary.

In more detail, the compounds of formula (I) can be manufactured by the methods given below, by the methods given in the examples or by analogous methods. Appropriate reaction conditions for the individual reaction steps are known to a person skilled in the art.

Starting materials are either commercially available or can be prepared by methods analogous to the methods given below, by methods described in references cited in the description or in the examples, or by methods known in the art.

A preferred embodiment of the process for preparing a compound of formula (I),

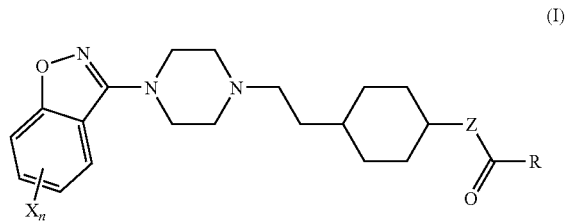

wherein Z is NH and R, X and n have meanings as given above, comprises one of the following steps:

a) reductive amination of an aldehyde of formula (I-1) with a 3-piperazine-1-yl-1,2-benzisoxazole of formula (I-2) in the presence of a reducing agent, and

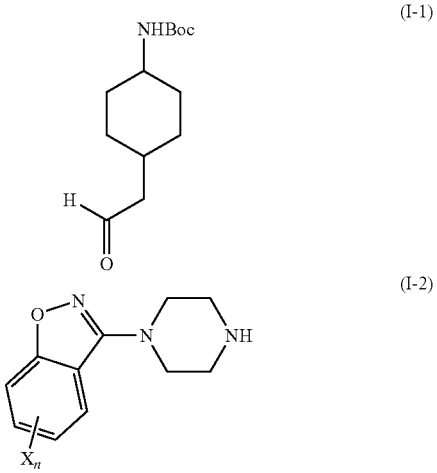

removing the Boc protecting group under acidic conditions to yield amine intermediate of formula (I-3)

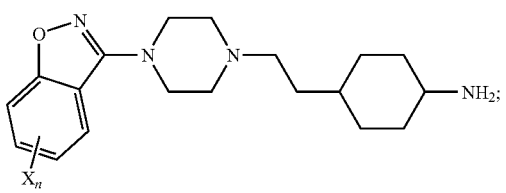

and
b) coupling of amine intermediate of formula (I-3) with a carboxylic acid R—COOH or acid chloride R—COCl to yield a compound of formula (I).

The ability of the compounds to bind to the $D_3$ receptors was determined using radioligand binding to cloned receptors selectively expressed in HEK-293 EBNA cells.

Biological Data

Membrane Preparation for Human $D_3$ Receptors

HEK-293 EBNA cells were transiently transfected with expression plasmids encoding for the human $D_3$ dopamine receptor. The cells were harvested 48 h post-transfection, washed three times with cold PBS and stored at −80° C. prior to use. The pellet was suspended in cold 50 mM Tris-HCl buffer containing 10 mM EDTA (pH 7.4) and homogenized with a Polytron (Kinematica AG, Basel, Switzerland) for 20-30 sec at 12.000 rpm. After centrifugation at 48.000×g for 30 mM at 4° C., the pellet was resuspended in cold 10 mM Tris-HCl buffer containing 0.1 mM EDTA (pH 7.4), homogenized, and centrifuged as above. This pellet was further resuspended in a smaller volume of ice cold 10 mM Tris-HCl buffer containing 0.1 mM EDTA (pH 7.4) and homogenized with a Polytron for 20-30 sec at 12.000 rpm. The protein content of this homogenate was determined with the Bio-Rad (radford) Protein Assay (Biorad Laboratories GmbH, München, Germany) according to the instructions of the manufacturer using gamma globulin as the standard. This homogenate was stored at −80° C. in aliquots and thawed immediately prior to use.

Radioligand Binding Assay Conditions

Aliquots of membrane preparations were thawed at RT, resuspended in assay buffer (50 mM Tris-HCl, 120 mM NaCl, 5 mM $MgCl_2$, 1 mM E TA, 5 mM KCl, 1.5 mM $CaCl_2$, pH=7.4), homogenized with a Polytron for 20-30 sec at 12.000 rpm and adjusted to a final concentration of approximately 7.5 μg protein/well.

The binding affinity (Ki) of the compounds was determined using radioligand binding. Membranes were incubated in a total volume of 200 with a fixed concentration of radioligand (final concentration approximately 0.5 nM [$^3$H]-spiperone) and ten concentrations of test compound in ranging between 10 μM-0.1 nM for 1 at RT. At the end of the incubation, the reaction mixtures were filtered on to unifilter 96-well white microplates with bonded GF/C filters (Packard Bio-Science, Zürich, Switzerland; preincubated for 1 h in 0.1% polyethylenimine (PEI) in assay buffer) with a Filtermate 196 harvester (Pack rd BioScience) and washed 3 times with cold assay buffer. The nonspecific binding was determined with equally composed reaction mixtures in the presence of 10 μM unlabelled spiperone. Per well 45 μl of Microscint 40 (Perkin Elmer, Schwerzenbach, Switzerland) was added, plate, for sealed, shaken for 20 mM and counted for 3 mM on a Topcount Microplate Scintillation Counter (Canberra Packard SA, Zürich, Switzerland) with quenching correction.

Data Calculation

The CPM value for each duplicate of a concentration of competing compound was averaged (y1), then the % specific binding was calculated according to the equation (((y1−nonspecific)/(total binding-non-specific))×100). Graphs were plotted with the % specific binding using XLfit, a curve fitting program that iteratively plots the data using Levenburg Marquardt algorithm. The single site competition analysis equation used was $y=A+((B-A)/(1+((x/C)^D)))$, where y is the % specific binding, A is the minimum y, B is the maximum y, C is the $IC_{50}$, x is the $\log_{10}$ of the concentration of the competing compound and D is the slope of the curve (the Hill Coefficient). From these curves the $IC_{50}$ (inhibition concentration at which 50% specific binding of the radioligand was displaced) and Hill coefficient were determined. The affinity constant (Ki) was calculated using the Cheng-Prusoff equation $Ki=(IC_{50}/1+([L]/Kd)$, where [L] is the concentration of radioligand and Kd is the dissociation constant of the radioligand at the receptor as determined by the saturation isotherm.

The compounds of the present invention are potent modulators of the dopamine $D_3$ receptors as is shown in the activity table hereinafter which gives the Ki values in μM for the dopamine $D_3$ receptors for some examples of the compounds of the present invention:

TABLE 1 acticity table: human Ki values of selected examples

| Ex. | Compound | Name | Ki dopamine D3 receptor: Human (D3) |
|---|---|---|---|
| 1 |  | N-(trans-4-{2-[4-(5,7-Difluoro-benzo[d]isoxazol-3-yl)-piperazin-1-yl]-ethyl}-cyclohexyl)-acetamide | 0.003702 |

TABLE 1-continued activity table: human Ki values of selected examples

| Ex. | Compound | Name | Ki dopamine D3 receptor: Human (D3) |
|---|---|---|---|
| 2 | | N-(trans-4-{2-[4-(5,7-Difluoro-benzo[d]isoxazol-3-yl)-piperazin-1-yl]-ethyl}-cyclohexyl)-2-hydroxy-acetamide | 0.003885 |
| 3 | | N-(trans-4-{2-[4-(5,7-Difluoro-benzo[d]isoxazol-3-yl)-piperazin-1-yl]-ethyl}-cyclohexyl)-2-methoxy-acetamide | 0.015558 |
| 4 | | N-(trans-4-{2-[4-(5,7-Difluoro-benzo[d]isoxazol-3-yl)-piperazin-1-yl]-ethyl}-cyclohexyl)-3-methoxy-propionamide | 0.003662 |
| 5 | | N-(trans-4-{2-[4-(5,7-Difluoro-benzo[d]isoxazol-3-yl)-piperazin-1-yl]-ethyl}-cyclohexyl)-2-(trans-4-methoxy-cyclohexyl)-acetamide | 0.011804 |
| 6 | | N-(trans-4-{2-[4-(5,7-Difluoro-benzo[d]isoxazol-3-yl)-piperazin-1-yl]-ethyl}-cyclohexyl)-propionamide | 0.004532 |

TABLE 1-continued activity table: human Ki values of selected examples

| Ex. | Compound | Name | Ki dopamine D3 receptor: Human (D3) |
|---|---|---|---|
| 7 | | 2-Cyclopropyl-N-(trans-4-{2-[4-(5,7-difluoro-benzo[d]isoxazol-3-yl)-piperazin-1-yl]-ethyl}-cyclohexyl)-acetamide | 0.002716 |
| 8 | | Tetrahydro-pyran-4-carboxylic acid (trans-4-{2-[4-(5,7-difluoro-benzo[d]isoxazol-3-yl)-piperazin-1-yl]-ethyl}-cyclohexyl)-amide | 0.009812 |
| 9 | | N-(trans-4-{2-[4-(5,7-Difluoro-benzo[d]isoxazol-3-yl)-piperazin-1-yl]-ethyl}-cyclohexyl)-malonamide | 0.005938 |
| 10 | | N-(trans-4-{2-[4-(4,5-Difluoro-benzo[d]isoxazol-3-yl)-piperazin-1-yl]-ethyl}-cyclohexyl)-acetamide | 0.008566 |
| 11 | | N-(trans-4-{2-[4-(4,5-Difluoro-benzo[d]isoxazol-3-yl)-piperazin-1-yl]-ethyl}-cyclohexyl)-3-methoxy-propionamide | 0.00971 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts and the like can be used, for example, as such as carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a process for the manufacture of pharmaceutical compositions. Such process comprises bringing the compound of formula I and/or pharmaceutically acceptable acid addition salt thereof and, if desired, one or more other therapeutically valuable substances into a galenical administration form together with one or more therapeutically inert carriers.

The dosage at which compounds of the invention can be administered can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

Synthesis

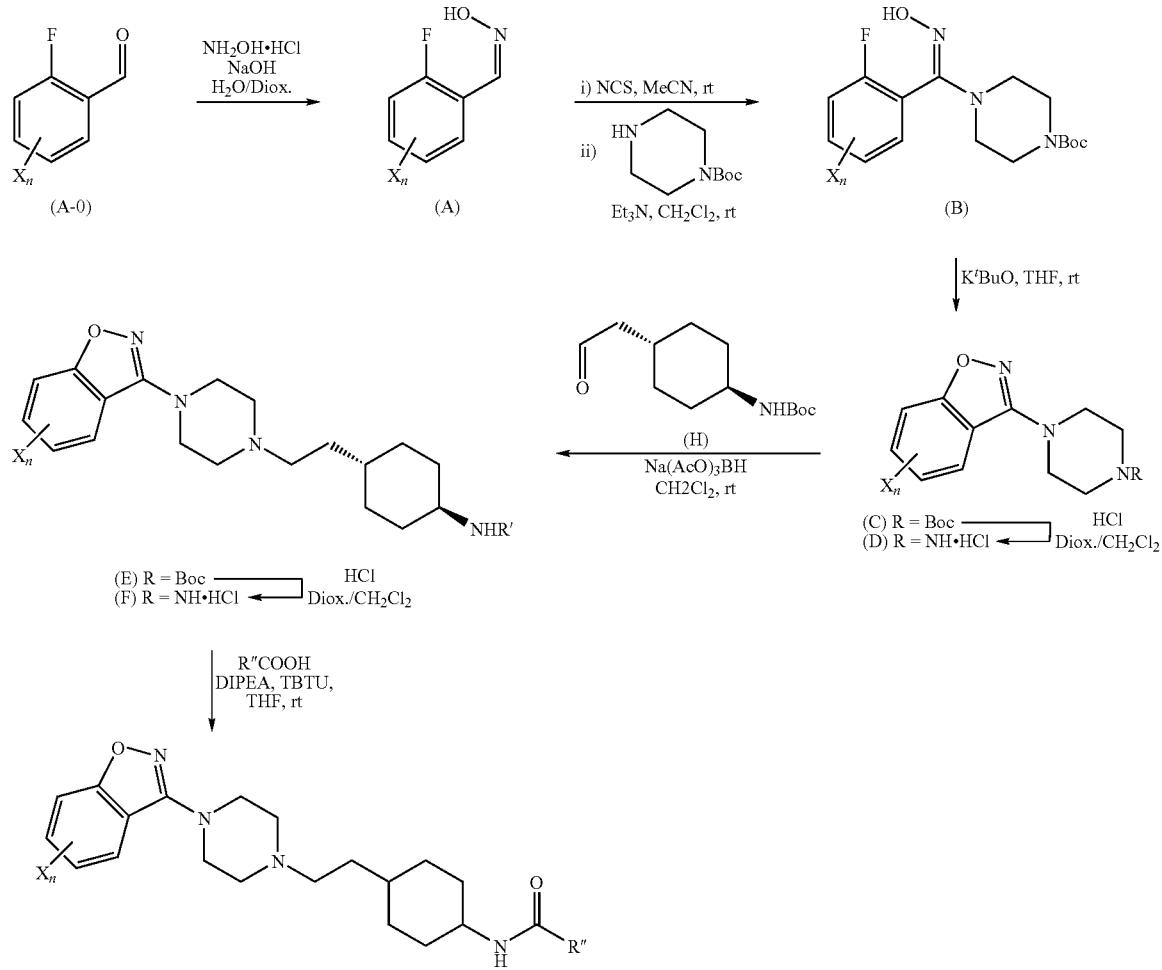

Scheme 1: General synthesis route

2-Fluoroaldehyde (A-0) is transformed into the corresponding 2-fluoro-benzaldehyde oxime (A) with hydroxylamine hydrochloride, followed by the reaction with tert-butyl 1-piperazinecarboxylate leading to the 4-(E,Z)-hydroxyimino]-(2-fluoro-phenyl)-methyl]-piperazine-1-carboxylic acid tert-butyl ester. Ring closure is performed with K$^t$BuO whereupon intermediate (C) is obtained. After the removal of protecting group Boc, (D) is reacted with trans-[4-(2-oxo-ethyl)-cyclohexyl]-carbamic acid tert-butyl ester leading to intermediate (F) via (E). The final product is obtained by reacting the free amino function with the desired carboxylic acid.

EXPERIMENTAL PART

The following examples are provided to further elucidate the invention.

Example 1

N-trans-(4-{2-[4-(5,7-Difluoro-benzo[d]isoxazol-3-yl)-piperazin-1-yl]-ethyl}-cyclohexyl)-acetamide

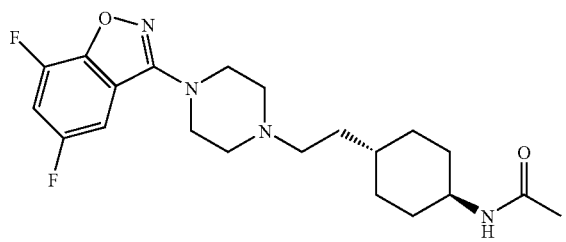

Step 1: 2,3,5-Trifluoro-benzaldehyde oxime (Intermediate A1)

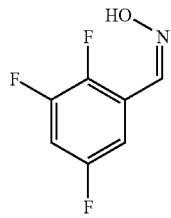

2,3,5-Trifluoroaldehyde (5.00 g, 31 mmol) was dissolved in EtOH (5 ml). H$_2$O (20 ml), ice (20 g) and hydroxylamine hydrochloride (2.39 g, 34 mmol) were added. To the resulting mixture was added over a period of 40 min a solution of NaOH (3.12 g, 78 mmol) in H$_2$O (40 ml). The resulting yellowish solution was stirred 2.5 h at r.t. before neutralisation with AcOH (pH=6). White crystals precipitated, were collected by filtration and washed with H$_2$O (50 ml). The product was dried 1 h at 50° C. and <20 mbar to yield 5.20 g (95%) of a white solid. m/z=174.0 ([M−H]$^−$).

Step 2: 4-[[(E,Z)-Hydroxyimino]-(2,3,5-trifluoro-phenyl)-methyl]-piperazine-1-carboxylic acid tert-butyl ester (Intermediate B1)

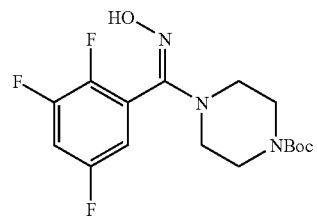

2,3,5-Trifluoro-benzaldehyde oxime (5.20 g, 30 mmol) was dissolved in MeCN (50 ml) and N-chlorosuccinimide (4.16 g, 31 mmol) was added in portions. The exothermic reaction rose the internal temperature to 42° C.

The yellow solution was stirred 30 min more before addition of H$_2$O and extraction with two portions of EtOAc. The organic layers were washed with more H$_2$O and brine and dried over Na$_2$SO$_4$. The solvent was evaporated to dryness and the residue was dissolved in CH$_2$Cl$_2$ (80 ml). Et$_3$N (4.15 ml, 31 mmol) was added to obtain a yellow solution. tert-Butyl 1-piperazinecarboxylate (6.64 g, 37 mmol) was added in portions and the resulting reaction mixture was stirred 1 h at r.t. Sat. aq. Na$_2$CO$_3$ was added and the product was extracted with CH$_2$Cl$_2$. After drying (Na$_2$SO$_4$) and evaporation of the solvent the product was purified by flash chromatography (100 g SiO$_2$, Hept/EtOAc 100:0→60:40) yielding 7.34 g (69%) of the title compound as a white solid. m/z=360.1 ([M+H]$^+$); 304.1 ([M+H−C$_4$H$_8$]$^+$).

Step 3: 4-(5,7-Difluoro-benzo[d]isoxazol-3-yl)-piperazine-1-carboxylic acid tert-butyl ester (Intermediate C1)

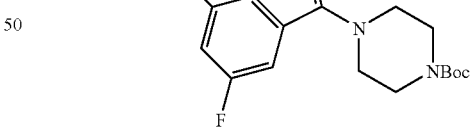

4-[[(E,Z)-Hydroxyimino]-(2,3,5-trifluoro-phenyl)-methyl]-piperazine-1-carboxylic acid tert-butyl ester (7.30 g, 20 mmol) was dissolved in THF (75 ml) and K$^t$BuO (2.51 g, 22 mmol) was added. The reaction mixture was stirred at r.t. over night before dilution with H$_2$O and extraction with two portions of EtOAc. The organic layers were washed with brine, dried (Na$_2$SO$_4$) and the solvent was evaporated. Flash chromatography (300 g SiO$_2$, Hept/EtOAc 100:0→75:25) yielded 1.69 (24%) of the title compound as white solid. m/z=340.1 ([M+H]$^+$); 284.1 ([M+H−C$_4$H$_8$]$^+$).

Step 4: 5,7-Difluoro-3-piperazin-1-yl-benzo[d]isoxazole hydrochloride (Intermediate D1)

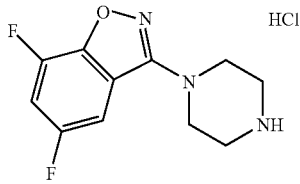

4-(5,7-Difluoro-benzo[d]isoxazol-3-yl)-piperazine-1-carboxylic acid tert-butyl ester (1.69 g, 5.0 mmol) was dissolved in $CH_2Cl_2$ (30 ml) and 4 N HCl in dioxane (24.9 ml, 100 mmol) was slowly added. The resulting mixture was stirred over night at r.t. After dilution with $^iPr_2O$ the product was collected by filtration and washed with one portion of $^iPr_2O$ before drying it under high vacuum at 50° C. to obtain 1.35 g (98%) as a white solid. m/z=240.1 ([M+H]$^+$).

Step 5: trans-(4-{2-[4-(5,7-Difluoro-benzo[d]isoxazol-3-yl)-piperazin-1-yl]-ethyl}-cyclo-hexyl)-carbamic acid tert-butyl ester (intermediate E1)

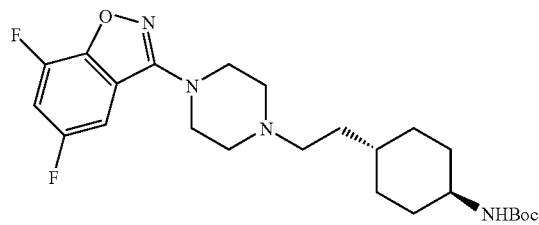

A solution in $CH_2Cl_2$ (20 ml) of 5,7-difluoro-3-piperazin-1-yl-benzo[d]isoxazole hydrochloride (1.35 g, 4.9 mmol) and trans-[4-(2-oxo-ethyl)-cyclohexyl]-carbamic acid tert-butyl ester (1.77 g, 7.3 mmol; prepared according to WO2007/093540) was stirred 15 min at r.t. before addition of Na(AcO)$_3$BH (1.87 g, 8.8 mmol). The reaction mixture was stirred 2 h at r.t., then sat. aq. $NaHCO_3$ was added and the product was extracted with 3 portions of $CH_2Cl_2$. After drying ($Na_2SO_4$) and evaporation of the solvent the product was purified by flash chromatography (50 g $SiO_2$, EtOAc/MeOH 100:0→90:10) to obtain 2.59 g (quant.) of title compound as a white solid. m/z=465.3 ([M+H]$^+$); 409.3 ([M+H−$C_4H_8$]$^+$).

Step 6: trans-4-{2-[4-(5,7-Difluoro-benzo[d]isoxazol-3-yl)-piperazin-1-yl]-ethyl}-cyclo-hexylamine hydrochloride (Intermediate F1)

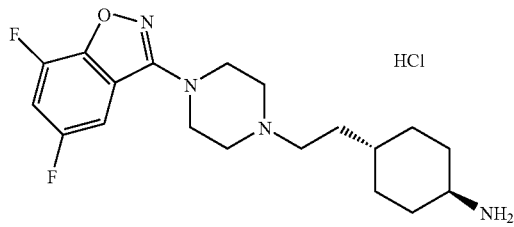

trans-(4-{2-[4-(5,7-Difluoro-benzo[d]isoxazol-3-yl)-piperazin-1-yl]-ethyl}-cyclohexyl)-carbamic acid tert-butyl ester (2.59 g, 5.6 mmol) was dissolved in $CH_2Cl_2$ (40 ml) and 4 N HCl in dioxane (27.9 ml, 112 mmol) was slowly added. The resulting mixture was stirred over night at r.t. After dilution with $^iPr_2O$ the product was collected by filtration and washed with one portion of $^iPr_2O$ before drying it under high vacuum at 50° C. to obtain 1.98 g (88%) as a white solid. m/z=365.2 ([M+H]$^+$).

Step 7: N-trans-(4-{2-[4-(5,7-Difluoro-benzo[d]isoxazol-3-yl)-piperazin-1-yl]-ethyl}-cyclohexyl)-acetamide trans-4-{2-[4-(5,7-Difluoro-benzo[d]isoxazol-3-yl)-piperazin-1-yl]-ethyl}-cyclohexylamine hydrochloride (150 mg, 0.37 mmol) was dissolved in THF and AcOH (31 mg, 0.52 mmol), $^iPr_2Net$ (193 mg, 1.5 mmol) and TBTU (144 m, 0.45 mmol) were added. The reaction mixture was stirred 2 h at r.t., then sat. aq. $NaHCO_3$ was added and the product was extracted with 2 portions of EtOAc. The organic layers were washed with brine, dried ($Na_2SO_4$) and the solvent was evaporated. Flash chromatography (20 g $SiO_2$, $CH_2Cl_2$/MeOH 100:0→80:20) yielded 100 mg (66%) of the title compound as white solid. m/z=407.3 ([M+H]$^+$).

Examples 2-9

Examples 2-9 were prepared in analogy to example 1 starting from trans-4-{2-[4-(5,7-difluoro-benzo[d]isoxazol-3-yl)-piperazin-1-yl]-ethyl}-cyclohexylamine hydrochloride (Intermediate F1) and an appropriate carboxylic acid.

TABLE 2 examples 2-9

| Ex. | Compound | Carboxylic acid | m/z ([M + H]$^+$) |
|---|---|---|---|
| 2 | N-(trans-4-{2-[4-(5,7-Difluoro-benzo[d]isoxazol-3-yl)-piperazin-1-yl]-ethyl}-cyclohexyl)-2-hydroxy-acetamide | from glycolic acid | 423.2 |
| 3 | N-(trans-4-{2-[4-(5,7-Difluoro-benzo[d]isoxazol-3-yl)-piperazin-1-yl]-ethyl}-cyclohexyl)-2-methoxy-acetamide | from methoxyacetic acid | 437.2 |
| 4 | N-(trans-4-{2-[4-(5,7-Difluoro-benzo[d]isoxazol-3-yl)-piperazin-1-yl]-ethyl}-cyclohexyl)-3-methoxy-propionamide | from 3-methoxypropionic acid | 451.2 |
| 5 | N-(trans-4-{2-[4-(5,7-Difluoro-benzo[d]isoxazol-3-yl)-piperazin-1-yl]-ethyl}-cyclohexyl)-2-(trans-4-methoxy-cyclohexyl)-acetamide | from (trans-4-methoxy-cyclohexyl)-acetic acid LiCl adduct | 519.4 |
| 6 | N-(trans-4-{2-[4-(5,7-Difluoro-benzo[d]isoxazol-3-yl)-piperazin-1-yl]-ethyl}-cyclohexyl)-propionamide | from propionic acid | 421.2 |
| 7 | 2-Cyclopropyl-N-(trans-4-{2-[4-(5,7-difluoro-benzo[d]isoxazol-3-yl)-piperazin-1-yl]-ethyl}-cyclohexyl)-acetamide | from cyclopropyl-acetic acid | 447.4 |
| 8 | Tetrahydro-pyran-4-carboxylic acid (trans-4-{2-[4-(5,7-difluoro-benzo[d]isoxazol-3-yl)-piperazin-1-yl]-ethyl}-cyclohexyl)-amide | from tetrahydropyran-4-yl-carboxylic acid | 477.3 |
| 9 | N-(trans-4-{2-[4-(5,7-Difluoro-benzo[d]isoxazol-3-yl)-piperazin-1-yl]-ethyl}-cyclohexyl)-malonamide | from methyl malonate monoamide | 450.3 |

Examples 10 and 11

Examples 10 and 11 were prepared in analogy to example 1 starting from trans-4-{2-[4-(4,5-difluoro-benzo[d]isoxazol-3-yl)-piperazin-1-yl]-ethyl}-cyclohexylamine hydrochloride (Intermediate F2) and an appropriate carboxylic acid.

TABLE 3 examples 10-11

| Ex. | Compound | Carboxylic acid | m/z ([M + H]$^+$) |
|---|---|---|---|
| 10 | N-(trans-4-{2-[4-(4,5-Difluoro-benzo[d]isoxazol-3-yl)-piperazin-1-yl]-ethyl}-cyclohexyl)-acetamide | from acetic acid | 407.3 |
| 11 | N-(trans-4-{2-[4-(4,5-Difluoro-benzo[d]isoxazol-3-yl)-piperazin-1-yl]-ethyl}-cyclohexyl)-3-methoxy-propionamide | from 3-methoxypropionic acid | 451.2 |

Synthesis of Intermediates trans-(4-Methoxy-cyclohexyl)-acetic acid lithium chloride adduct

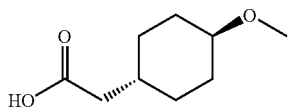

Step 1: trans-(4-Hydroxy-cyclohexyl)-acetic acid

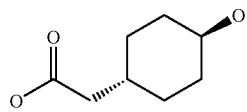

The title compound can be prepared in accordance with literature *Journal of the American Chemical Society* (1948), 70 1898-9.

Step 2: trans-(4-Hydroxy-cyclohexyl)-acetic acid methyl ester

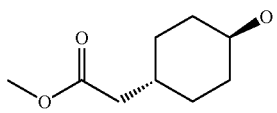

The ester can be prepared by refluxing the corresponding acid in methanol and catalytic sulfuric acid for 4 hours.

Step 3: trans-(4-methoxy-cyclohexyl)-acetic acid methyl ester

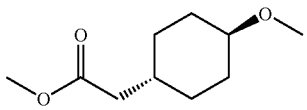

trans-(4-Hydroxy-cyclohexyl)-acetic acid methyl ester (500 mg, 2.90 mmol) were dissolved in 1.5 ml DMF and cooled to 0-5° C. Sodium hydride (190 mg, 4.35 mmol, 55%) and iodomethane (3.62 ml, 23.2 mmol) were added and the reaction mixture stirred for 4 hours at 0-5° C. The reaction mixture was quenched with saturated NaHCO3-solution and extracted with dichloromethane. The organic extract was washed with brine, dried with sodium sulfate, filtered and evaporated. The crude product (561 mg, quant.) was obtained as a colourless oil and used without any further purification for the next step.

Step 4: trans-(4-Methoxy-cyclohexyl)-acetic acid lithium chloride adduct trans-(4-Methoxy-cyclohexyl)-acetic acid methyl ester (600 mg, 3.22 mmol) was dissolved in a mixture of THF (8 ml), MeOH (4 ml) and H$_2$O (4 ml). LiOH.H$_2$O (270 mg, 6.44 mmol) was added ant the reaction mixture was stirred over night at r.t. After evaporation of the solvents and acidifying the residue with 2 N HCl, the product was obtained as LiCl adduct by full evaporation. Yield: 600 mg (72%). White solid.

Intermediate F2 trans-4-{2-[4-(4,5-Difluoro-benzo[d]isoxazol-3-yl)-piperazin-1-yl]-ethyl}-cyclohexylamine hydrochloride

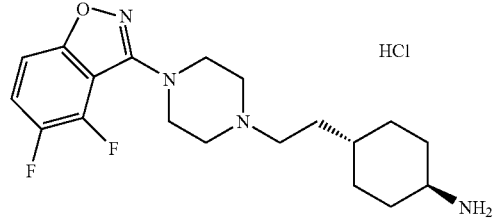

The title compound was prepared in analogy to trans-(4-{2-[4-(5,7-difluoro-benzo[d]isoxazol-3-yl)-piperazin-1-yl]-ethyl}-cyclohexyl)-carbamic acid (Intermediate F1) starting from 2,3,6-trifluorobenzaldehyde.

Pharmaceutical Preparations

Example A

Film coated tablets containing the following ingredients can be manufactured in a conventional manner:

TABLE 4

Example of film coated tablets

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

TABLE 5

Example of capsules

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

TABLE 6

Example of injection solutions

| Compound of formula (I) | 3.0 mg |
|---|---|
| Gelatine | 150.0 mg |
| Phenol | 4.7 mg |
| Sodium carbonate | to obtain a final pH of 7 |
| Water for injection solutions | ad 1.0 ml |

Example D

Soft gelatin capsules containing the following ingredients can be manufactured in a conventional manner:

TABLE 7

Example of soft gelatin capsules

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

TABLE 8

Example of sachets

| Compound of formula (I) | 50.0 mg |
|---|---|
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

The invention claimed is:

1. A compound of formula (I):

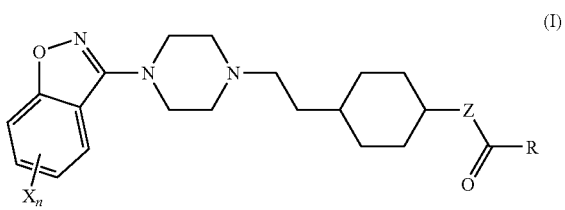

wherein:
X is independently fluorine or chlorine;
n is 1 or 2;
Z is —NH— or —O—;
R is $C_{1-6}$-alkyl, wherein $C_{1-6}$-alkyl is optionally substituted by —CONH$_2$, 3 to 6 membered monocyclic cycloalkyl or 4 to 6 membered monocyclic heterocycloalkyl;
$C_{1-6}$-hydroxyallyl;
$C_{1-6}$-alkoxy;
3 to 6 membered monocyclic cycloalkyl; or
4 to 6 membered monocyclic heterocycloalkyl;

wherein 3 to 6 membered monocyclic cycloalkyl and 4 to 6 membered monocyclic heterocycloalkyl are optionally substituted by one or more substituents selected from the group consisting of halo, hydroxy, $C_{1-6}$-alkyl, $C_{1-6}$-haloalkyl, $C_{1-6}$-hydroxyalkyl and $C_{1-6}$-alkoxy;
or a pharmaceutically acceptable salt thereof.

2. The compound of claim 1, wherein Z is —NH—.
3. The compound of claim 1, wherein Z is —O—.
4. The compound of claim 1, wherein n is 1.
5. The compound of claim 1, wherein n is 2.
6. The compound of claim 1, wherein X is fluorine.
7. The compound of claim 1, wherein X is chlorine.
8. The compound of claim 1, having formula (I'):

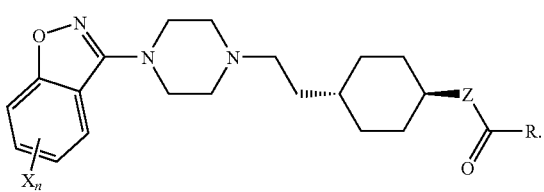

(I')

9. The compound of claim 1 having formula (Ia) or formula (Ia'):

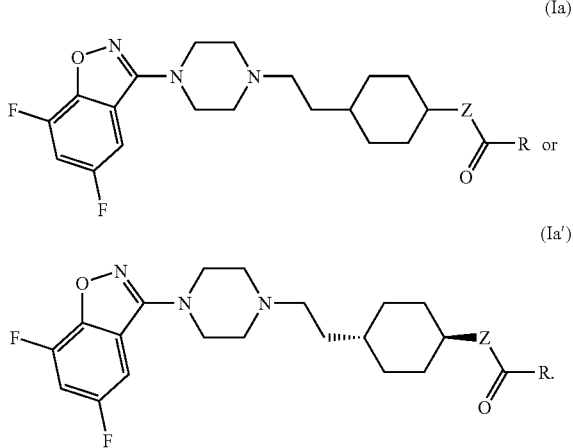

10. The compound of claim 9 selected from the group consisting of:
N-(trans-4-{2-[4-(5,7-Difluoro-benzo[d]isoxazol-3-yl)-piperazin-1-yl]-ethyl}-cyclohexyl)-acetamide;
N-(trans-4-{2-[4-(5,7-Difluoro-benzo[d]isoxazol-3-yl)-piperazin-1-yl]-ethyl}-cyclohexyl)-2-hydroxy-acetamide;
N-(trans-4-{2-[4-(5,7-Difluoro-benzo[d]isoxazol-3-yl)-piperazin-1-yl]-ethyl}-cyclohexyl)-2-methoxy-acetamide;
N-(trans-4-{2-[4-(5,7-Difluoro-benzo[d]isoxazol-3-yl)-piperazin-1-yl]-ethyl}-cyclohexyl)-3-methoxy-propionamide;
N-(trans-4-{2-[4-(5,7-Difluoro-benzo[d]isoxazol-3-yl)-piperazin-1-yl]-ethyl}-cyclohexyl)-2-(trans-4-methoxy-cyclohexyl)-acetamide;
N-(trans-4-{2-[4-(5,7-Difluoro-benzo[d]isoxazol-3-yl)-piperazin-1-yl]-ethyl}-cyclohexyl)-propionamide;
2-Cyclopropyl-N-(trans-4-{2-[4-(5,7-difluoro-benzo[d]isoxazol-3-yl)-piperazin-1-yl]-ethyl}-cyclohexyl)-acetamide;

Tetrahydro-pyran-4-carboxylic acid (trans-4-{2-[4-(5,7-difluoro-benzo[d]isoxazol-3-yl)-piperazin-1-yl]-ethyl}-cyclohexyl)-amide; and
N-(trans-4-{2-[4-(5,7-Difluoro-benzo[d]isoxazol-3-yl)-piperazin-1-yl]-ethyl}-cyclohexyl)-malonamide.

11. The compound of claim 1 having formula (Ib) or formula (Ib'):

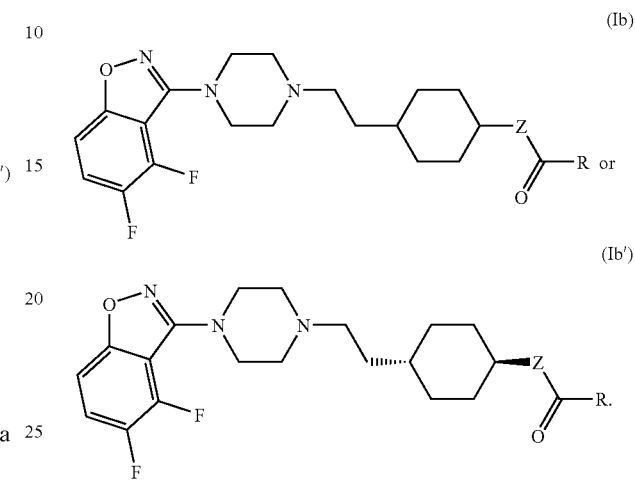

12. The compound of claim 11 selected from the group consisting of:
N-(trans-4-{2-[4-(4,5-Difluoro-benzo[d]isoxazol-3-yl)-piperazin-1-yl]-ethyl}-cyclohexyl)-acetamide and
N-(trans-4-{2-[4-(4,5-Difluoro-benzo[d]isoxazol-3-yl)-piperazin-1-yl]-ethyl}cyclohexyl)-3-methoxy-propionamide.

13. The compound of claim 1, wherein R is methyl, hydroxy-methyl, methoxy-methyl, methoxy-ethyl, methoxy-cyclohexyl-methyl, ethyl, cyclopropyl-methyl, tetrahydropyranyl or $CONH_2$-methyl.

14. The compound of claim 1, wherein R is $C_{1-6}$-alkyl optionally substituted with $CONH_2$, optionally substituted 3 to 6 monocyclic cycloalkyl, or optionally substituted 4 to 6 monocyclic heterocycloalkyl.

15. The compound of claim 14, wherein R is $C_{1-6}$-alkyl.
16. The compound of claim 15, wherein R is methyl.
17. The compound of claim 15, wherein R is ethyl.
18. The compound of claim 14, wherein R is $C_{1-6}$-alkyl substituted by —$CONH_2$, optionally substituted 3 to 6 membered monocyclic cycloalkyl or optionally substituted 4 to 6 membered monocyclic heterocycloalkyl.
19. The compound of claim 18, wherein R is $C_{1-6}$-alkyl substituted by —$CONH_2$.
20. The compound of claim 19, wherein R is $CONH_2$-methyl.
21. The compound of claim 18, wherein R is $C_{1-6}$-alkyl substituted by 3 to 6 membered monocyclic cycloalkyl.
22. The compound of claim 21, wherein R is cyclopropyl-methyl.
23. The compound of claim 18, wherein R is $C_{1-6}$-alkyl substituted by 3 to 6 membered monocyclic cycloalkyl wherein the 3 to 6 membered monocyclic cycloalkyl is substituted by one or more substituents selected from the group consisting of halo, hydroxyl, $C_{1-6}$-alkyl, $C_{1-6}$-haloalkyl, $C_{1-6}$-hydroxyalkyl and $C_{1-6}$-alkoxy.
24. The compound of claim 23, wherein R is $C_{1-6}$-alkyl substituted by 3 to 6 monocyclic cycloalkyl, which 3 to 6 membered monocyclic cycloalkyl is substituted by halo.

25. The compound of claim 23, wherein R is $C_{1-6}$-alkyl substituted by 3 to 6 membered monocyclic cycloalkyl, which 3 to 6 membered monocyclic cycloalkyl is substituted by hydroxy.

26. The compound of claim 23, wherein R is $C_{1-6}$-alkyl substituted by 3 to 6 membered monocyclic cycloalkyl, which 3 to 6 membered monocyclic cycloalkyl is substituted by $C_{1-6}$-alkoxy.

27. The compound of claim 26, wherein R is methoxy-cyclohexyl-methyl.

28. The compound of claim 23, wherein R is $C_{1-6}$-alkyl substituted by 3 to 6 membered monocyclic cycloalkyl, which 3 to 6 membered monocyclic cycloalkyl is substituted by $C_{1-6}$-alkyl.

29. The compound of claim 23, wherein R is $C_{1-6}$-allyl substituted by 3 to 6 membered monocyclic cycloalkyl, which 3 to 6 membered monocyclic cycloalkyl is substituted by $C_{1-6}$-haloalkyl.

30. The compound of claim 23, wherein R is $C_{1-6}$-alkyl substituted by 3 to 6 membered monocyclic cycloalkyl, which 3 to 6 membered monocyclic cycloalkyl is substituted by $C_{1-6}$-hydroxyalkyl.

31. The compound of claim 18, wherein R is $C_{1-6}$-alkyl substituted by 4 to 6 membered monocyclic heterocycloalkyl, wherein the 4 to 6 membered monocyclic heterocycloalkyl is substituted by one or more substituents selected from the group consisting of halo, hydroxyl, $C_{1-6}$-allyl, $C_{1-6}$-haloalkyl, $C_{1-6}$-hydroxyalkyl and $C_{1-6}$-alkoxy.

32. The compound of claim 31, wherein R is $C_{1-6}$-alkyl substituted by 4 to 6 membered monocyclic heterocycloalkyl, wherein the 4 to 6 membered monocyclic heterocycloalkyl is substituted by halo.

33. The compound of claim 31, wherein R is $C_{1-6}$-alkyl substituted by 4 to 6 membered monocyclic heterocycloalkyl, wherein the 4 to 6 membered monocyclic heterocycloalkyl is substituted by hydroxyl.

34. The compound of claim 31, wherein R is $C_{1-6}$-alkyl substituted by 4 to 6 membered monocyclic heterocycloalkyl, wherein the 4 to 6 membered monocyclic heterocycloalkyl is substituted by $C_{1-6}$-alkyl.

35. The compound of claim 31, wherein R is $C_{1-6}$-alkyl substituted by 4 to 6 membered monocyclic heterocycloalkyl, wherein the 4 to 6 membered monocyclic heterocycloalkyl is substituted by $C_{1-6}$-haloalkyl.

36. The compound of claim 31, wherein R is $C_{1-6}$-alkyl substituted by 4 to 6 membered monocyclic heterocycloalkyl, wherein the 4 to 6 membered monocyclic heterocycloalkyl is substituted by $C_{1-6}$-hydroxyalkyl.

37. The compound of claim 31, wherein R is $C_{1-6}$-alkyl substituted by 4 to 6 membered monocyclic heterocycloalkyl, wherein the 4 to 6 membered monocyclic heterocycloalkyl is substituted by $C_{1-6}$-alkoxy.

38. The compound of claim 18, wherein R is $C_{1-6}$-alkyl substituted by 4 to 6 membered monocyclic heterocycloalkyl.

39. The compound of claim 1, wherein R is $C_{1-6}$-hydroxyalkyl.

40. The compound of claim 1, wherein R is $C_{1-6}$-alkoxy.

41. The compound of claim 1, wherein R is 3 to 6 membered monocyclic cycloalkyl optionally substituted by one or more substituents selected from the group consisting of halo, hydroxyl, $C_{1-6}$-alkyl, $C_{1-6}$-haloalkyl, $C_{1-6}$-hydroxyallyl and $C_{1-6}$-alkoxy.

42. The compound of claim 41, wherein R is 3 to 6 membered monocyclic cycloalkyl.

43. The compound of claim 41, wherein R is 3 to 6 membered monocyclic cycloalkyl substituted by one or more substituents selected from the group consisting of halo, hydroxyl, $C_{1-6}$-alkyl, $C_{1-6}$-haloalkyl, $C_{1-6}$-hydroxyalkyl and $C_{1-6}$-alkoxy.

44. The compound of claim 43, wherein R is 3 to 6 membered monocyclic cycloalkyl substituted by halo.

45. The compound of claim 43, wherein R is 3 to 6 membered monocyclic cycloalkyl substituted by hydroxyl.

46. The compound of claim 43, wherein R is 3 to 6 membered monocyclic cycloalkyl substituted by $C_{1-6}$-alkyl.

47. The compound of claim 43, wherein R is 3 to 6 membered monocyclic cycloalkyl substituted by $C_{1-6}$-haloalkyl.

48. The compound of claim 43, wherein R is 3 to 6 membered monocyclic cycloalkyl substituted by $C_{1-6}$-hydroxyalyl.

49. The compound of claim 43, wherein R is 3 to 6 membered monocyclic cycloalkyl substituted by $C_{1-6}$-alkoxy.

50. The compound of claim 1, wherein R is 4 to 6 membered monocyclic heterocycloalkyl optionally substituted by one or more substituents selected from the group consisting of halo, hydroxyl, $C_{1-6}$-alkyl, $C_{1-6}$-haloalkyl, $C_{1-6}$-hydroxyalkyl and $C_{1-6}$-alkoxy.

51. The compound of claim 50, wherein R is 4 to 6 membered monocyclic heterocycloalkyl.

52. The compound of claim 50, wherein R is 4 to 6 membered monocyclic heterocycloalkyl substituted by one or more substituents selected from the group consisting of halo, hydroxyl, $C_{1-6}$-alkyl, $C_{1-6}$-haloalkyl, $C_{1-6}$-hydroxyalkyl and $C_{1-6}$-alkoxy.

53. The compound of claim 52, wherein R is 4 to 6 membered monocyclic heterocycloalkyl substituted by halo.

54. The compound of claim 52, wherein R is 4 to 6 membered monocyclic heterocycloalkyl substituted by hydroxyl.

55. The compound of claim 52, wherein R is 4 to 6 membered monocyclic heterocycloalkyl substituted by $C_{1-6}$-alkyl.

56. The compound of claim 52, wherein R is 4 to 6 membered monocyclic heterocycloalkyl substituted by $C_{1-6}$-haloalkyl.

57. The compound of claim 52, wherein R is 4 to 6 membered monocyclic heterocycloalkyl substituted by $C_{1-6}$-hydroxyalkyl.

58. The compound of claim 52, wherein R is 4 to 6 membered monocyclic heterocycloalkyl substituted by $C_{1-6}$-alkoxy.

59. A pharmaceutical composition comprising a therapeutically effective amount of a compound of formula I

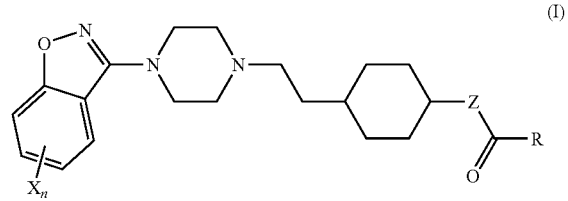

wherein:
X is independently fluorine or chlorine;
n is 1 or 2;
Z is —NH— or —O—;

R is $C_{1-6}$-alkyl, wherein $C_{1-6}$-allyl is optionally substituted by —$CONH_2$, 3 to 6 membered monocyclic cycloalkyl or 4 to 6 membered monocyclic heterocycloalkyl;

$C_{1-6}$-hydroxyalkyl;

$C_{1-6}$-alkoxy;

3 to 6 membered monocyclic cycloalkyl; or 4 to 6 membered monocyclic heterocycloalkyl;

wherein 3 to 6 membered monocyclic cycloalkyl and 4 to 6 membered monocyclic heterocycloalkyl are optionally substituted by one or more substituents selected from the group consisting of halo, hydroxy, $C_{1-6}$-alkyl, $C_{1-6}$-haloalkyl, $C_{1-6}$-hydroxyallyl and $C_{1-6}$-alkoxy;

or a pharmaceutically acceptable salt thereof and a pharmaceutically acceptable carrier.

\* \* \* \* \*